(12) United States Patent
Claude

(10) Patent No.: US 6,780,424 B2
(45) Date of Patent: Aug. 24, 2004

(54) CONTROLLED MORPHOLOGIES IN POLYMER DRUG FOR RELEASE OF DRUGS FROM POLYMER FILMS

(76) Inventor: Charles David Claude, 14760 McVay, San Jose, CA (US) 95127

( * ) Notice: Subject to any disclaimer, the term of this patent is extended or adjusted under 35 U.S.C. 154(b) by 0 days.

(21) Appl. No.: 09/822,952

(22) Filed: Mar. 30, 2001

(65) Prior Publication Data

US 2002/0142039 A1 Oct. 3, 2002

(51) Int. Cl.$^7$ .................................................. A61F 2/00
(52) U.S. Cl. ...................................... 424/423; 427/2.3
(58) Field of Search ............................ 424/423; 427/2.3

(56) References Cited

U.S. PATENT DOCUMENTS

| | | | |
|---|---|---|---|
| 2,072,303 A | 3/1937 | Herrmann et al. | 128/335.5 |
| 4,882,168 A | 11/1989 | Casey et al. | 424/468 |
| 4,977,901 A | 12/1990 | Ofstead | 128/772 |
| 5,292,516 A | 3/1994 | Viegas et al. | 424/423 |
| 5,298,260 A | 3/1994 | Viegas et al. | 424/486 |
| 5,300,295 A | 4/1994 | Viegas et al. | 424/427 |
| 5,306,501 A | 4/1994 | Viegas et al. | 424/423 |
| 5,328,471 A | 7/1994 | Slepian | 604/101 |
| 5,330,768 A | 7/1994 | Park et al. | 424/501 |
| 5,462,990 A | 10/1995 | Hubbell et al. | 525/54.1 |
| 5,464,650 A | 11/1995 | Berg et al. | 427/2.3 |
| 5,578,073 A | 11/1996 | Haimovich et al. | 623/1 |
| 5,605,696 A * | 2/1997 | Eury et al. | 424/423 |
| 5,628,730 A | 5/1997 | Shapland et al. | 604/21 |
| 5,658,995 A | 8/1997 | Kohn et al. | 525/432 |
| 5,667,767 A | 9/1997 | Greff et al. | 424/9.411 |
| 5,670,558 A | 9/1997 | Onishi et al. | 523/112 |
| 5,700,286 A | 12/1997 | Tartaglia et al. | 623/1 |
| 5,716,981 A | 2/1998 | Hunter et al. | 514/449 |
| 5,746,998 A | 5/1998 | Torchilin et al. | 424/9.4 |
| 5,800,392 A | 9/1998 | Racchini | 604/96 |
| 5,824,049 A | 10/1998 | Ragheb et al. | 623/1 |
| 5,830,178 A | 11/1998 | Jones et al. | 604/49 |
| 5,837,313 A | 11/1998 | Ding et al. | 427/2.21 |
| 5,851,508 A | 12/1998 | Greff et al. | 424/9.411 |
| 5,865,814 A | 2/1999 | Tuch | 604/265 |
| 5,873,904 A | 2/1999 | Ragheb et al. | 623/1 |

(List continued on next page.)

FOREIGN PATENT DOCUMENTS

| | | |
|---|---|---|
| EP | 0 665 023 | 8/1995 |
| EP | 0 970 711 | 1/2000 |
| WO | WO 91/12846 | 9/1991 |
| WO | WO 97/45105 | 12/1997 |
| WO | WO 99/63981 | 12/1999 |
| WO | WO 00/12147 | 3/2000 |
| WO | WO 00/64506 | 11/2000 |
| WO | WO 01/01890 | 1/2001 |
| WO | WO 01/17577 | 3/2001 |
| WO | WO 01/45763 | 6/2001 |
| WO | WO 01/74414 | 10/2001 |

OTHER PUBLICATIONS

Aoyagi, T., et al., "Preparation of cross–linked aliphatic polyester and application to thermo–responsive material", *Journal of Controlled Release*, vol. 32, 87–96, (1994).

(List continued on next page.)

*Primary Examiner*—Shelley A. Dodson
*Assistant Examiner*—Konata M George
(74) *Attorney, Agent, or Firm*—Squire, Sanders & Dempsey

(57) ABSTRACT

A drug delivery system is provided including a bulk polymer phase and a polymeric drug-enriched phase within the bulk polymer phase. At least one drug is incorporated into the drug-enriched phase. The system can be used, for example, on implantable medical devices such as stents.

16 Claims, 1 Drawing Sheet

U.S. PATENT DOCUMENTS

| | | | |
|---|---|---|---|
| 5,925,720 A | 7/1999 | Kataoka et al. | 525/523 |
| 5,955,509 A | 9/1999 | Webber et al. | 514/772.7 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 6,001,382 A | 12/1999 | Levy | 424/405 |
| 6,010,530 A | 1/2000 | Goicoechea | 623/1 |
| 6,015,541 A | 1/2000 | Greff et al. | 424/1.25 |
| 6,060,518 A | 5/2000 | Kabanov et al. | 514/781 |
| 6,096,070 A | 8/2000 | Ragheb et al. | 623/1 |
| 6,153,252 A * | 11/2000 | Hossainy et al. | 427/2.3 |
| 6,165,212 A | 12/2000 | Dereume et al. | 623/1.13 |

OTHER PUBLICATIONS

Chung, J.E., et al., "Inner core segment design for drug delivery control of thermo–responsive polymeric micelles", *Journal of Controlled Release*, vol. 65, 93–103, (2000).

Inoue, T., et al., "An AB block copolymer of oligo(methyl methacrylate) and poly(acrylic acid) for micellar delivery of hydrophobic drugs", *Journal of Controlled Release*, vol. 51, 221–229, (1998).

Kataoka, K., et al., "Block copolymer micelles as vehicles for drug delivery", *Journal of Controlled Release*, vol. 24, 119–132 (1993).

Liu, H., et al., "Drug release characteristics of unimolecular polymeric micelles", *Journal of Controlled Release*, vol. 68, 167–174, (2000).

Yokoyama, M., et al., "Characterization of physical entrapment and chemical conjugation of adriamycin in polymeric micelles and their design for in vivo delivery to a solid tumor", *Journal of Controlled Release*, vol. 50, 79–92, (1998).

Barath et al., *Low Dose of Antitumor Agents Prevents Smooth Muscle Cell Proliferation After Endothelial Injury*; JACC vol. 13, No. 2; Feb. 1989:252A (Abstract).

Matsumaru et al., *Embolic Materials For Endovascular Treatment of Cerebral Lesions*; J. Biomater. Sci. Polymer Edn, vol. 8, No. 7 (1997), pp. 555–569.

Miyazaki et al., *Antitumor Effect of Implanted Ethylene–Vinyl Alcohol Copolymer Matrices Containing Anticancer Agents on Ehrlich Ascites Carcinoma and P388 Leukemia in Mice*, Chem. Pharm. Bull. 33(6) (1985), pp. 2490–2498.

Miyazawa et al., *Effects of Pemirolast and Tranilast on Intimal Thickening After Arterial Injury in the Rat*; J. Cardiovasc. Pharmacol. (1997), pp. 157–162.

Ohsawa et al.; *Preventive Effects of an Antiallergic Drug, Pemirolast Potassium, on Restenosis After Percutaneous Transluminal Coronary Angioplasty*; American Heart Journal (Dec. 1998); pp. 1081–1087.

Pechar et al., *Poly(ethylene glycol) Multiblock Copolymer as a Carrier of Anti–Cancer Drug Doxorubicin*, Bioconjugate Chemistry, Mar/Apr. 2000, pp. 131–139; vol. 11, No. 2, Published by American Chemical Society.

Shigeno, *Prevention of Cerebrovascular Spasm by Bosentan, Novel Endothelin Receptor*; Chemical Abstract 125:212307 (1996).

Marconi et al., *Covalent bonding of heparin to a vinyl copolymer for biomedical applications*, Biomaterials, 18(12):885–890 (1997).

* cited by examiner

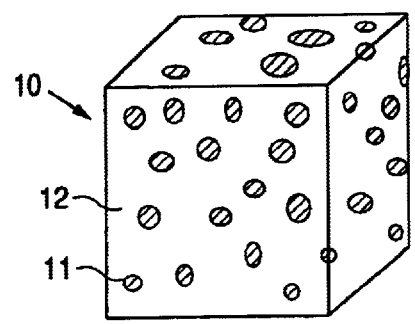
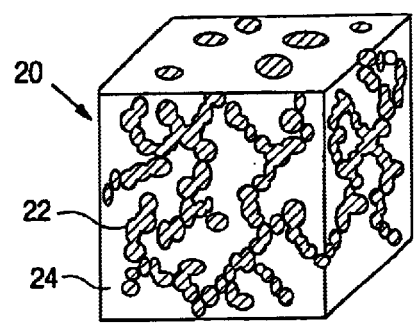
FIG. 1  FIG. 2
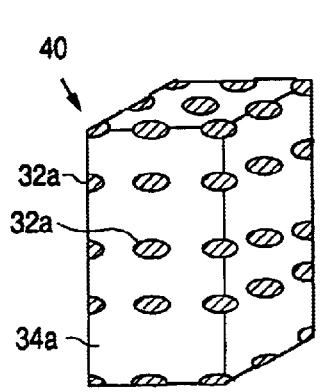
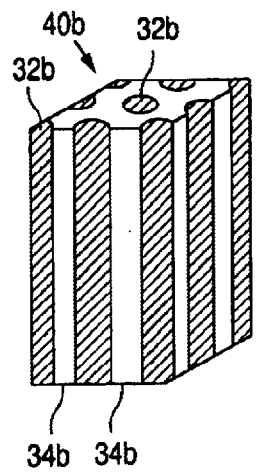
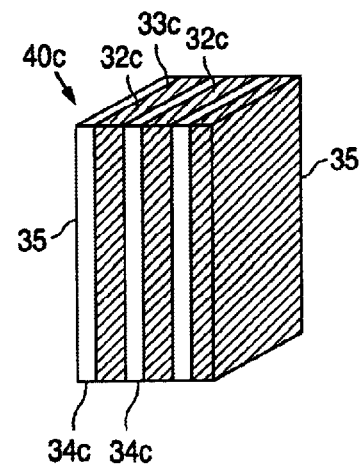
FIG. 3a  FIG. 3b  FIG. 3c

_US 6,780,424 B2_

CONTROLLED MORPHOLOGIES IN POLYMER DRUG FOR RELEASE OF DRUGS FROM POLYMER FILMS

BACKGROUND OF THE INVENTION

The present invention relates to a system for controlled drug release within a vessel lumen, and to a method and to a device for controlled drug release.

A device for providing a continuous release of drugs over an extended period of time following from a single administration of a drug releasing material has wide application in treating disease. One type of continuous drug release mechanism is based upon degradation of biodegradable polymers. The biodegradable polymers have drugs incorporated within them. As the biodegradable polymers hydrolyze over time, the drugs are released. Hydroxycarboxylic acid polymers have been used to release drugs in this manner.

One other modality of drug release is a prolonged, though discontinuous release of drugs. Frequently, with a discontinuous release, there is a lag phase of no or negligible drug release when a drug delivery device is delivered to an in situ site for drug release.

One problem with sustaining drug release is that when drugs, particularly water soluble drugs, are incorporated into polymers, it is difficult to prevent a rapid, uncontrolled release of the drugs. As used herein, the term "water soluble drug" is defined as a hydrophilic compound with a solubility in water greater than 1 percent (w/v) and that is practically insoluble in nonpolar organic solvents such as ethyl acetate, methylene chloride, chloroform, toluene, or hydrocarbons. This rapid, uncontrolled release from a drug-polymeric matrix is known as a "burst effect." The burst effect is particularly troublesome with high drug loading.

One other type of uncontrolled drug release is characterized by a "lag effect." The lag effect occurs when the rate of drug release decreases to a negligible value.

The degree of drug release from a polymeric-drug matrix is, in part, controlled by the morphology of the polymeric-drug matrix. The morphology is, for some embodiments, a single-phase dispersion and for other embodiments, is a multi-phase dispersion. A single-phase dispersion is typically transparent when viewed in natural light. The single phase dispersion is clear and transparent because both the drug and the polymer have a mutual miscibility. A multi-phase dispersion has micro domains that give the dispersion a cloudy appearance. For some multi-phase dispersions, drugs are embedded in a polymeric matrix as particles.

Drug release is also controlled by the degree of drug loading. Matrices that have dispersed drug particles that do not contact each other tend to have a slow release of drug. A drug carrier such as blood is typically required to move the drug through the matrix and into the bloodstream of a living being.

Drug-polymeric matrices have been used to deliver drugs in situ through a vehicle such as a stent. The drug-polymeric matrix has been applied as a coating or a wrap to the stent. U.S. Pat. No. 5,605,696, which issued Feb. 25, 1997, describes a drug loaded polymeric material that is applied to an intravascular stent. The drug-polymeric matrix defines pores, multilayered to permit a combination of different drugs in a single stent. The stent also includes a rate controlling membrane that controlled retention and delivery of selected drugs to the affected blood vessel. The drug is dispersed as small particles, having a maximum cross-sectional dimension of 10 microns.

DESCRIPTION OF THE DRAWINGS

FIG. 1 is a perspective view of one embodiment of the drug delivery system of the present invention wherein a system component is below the percolation threshold.

FIG. 2 is a perspective view of one embodiment of the drug delivery system of the present invention wherein a system component is above the percolation threshold.

FIG. 3a is a perspective view of the drug delivery system of the present invention wherein the pore structure is discontinuous.

FIG. 3b is a perspective view of the drug delivery system of the present invention wherein the pore structure is semi-continuous.

FIG. 3c is a perspective view of another embodiment of the drug delivery system of the present invention wherein the pore structure is continuous.

SUMMARY OF THE INVENTION

One embodiment of the present invention includes a drug release system. The drug release system releases one or more drugs when implanted in a human being or other vertebrate but does not display a substantial release of drugs when outside of the human being or other vertebrates. The drug release system comprises a bulk polymer phase and a polymeric drug-enriched phase within the bulk polymer phase. The drug release system also includes at least one drug that is incorporated in the polymeric drug-enriched phase. The drug release system of the present invention releases one or more drugs in situ while decreasing the rate of release of the drug when the device is not in situ. The drug profile release is predictable and preselectable.

Another embodiment of the present invention includes a coating that comprises a drug release system. The drug release system has desirable film properties which render it useful as a coating for an implantable device. The present invention also includes an implantable device with a coating that is adhered to the implantable device. The coated implantable device releases one or more drugs in a predictable and preselectable manner when implanted in a human being or other vertebrate.

Another embodiment of the present invention includes a method for substantially continuously releasing drugs. The method includes attaching or adhering a drug delivery system to an implantable medical device. The drug delivery system comprises a bulk polymer phase and a polymeric drug-enriched phase within the bulk polymer phase. The drug release system also includes one or more drugs that are incorporated in the polymeric drug-enriched phase.

One other embodiment includes a device for continuously and predictably releasing drugs. The device comprises a drug release system that comprises a bulk polymer phase. The drug release system also includes a drug-enriched polymeric phase within the bulk polymer phase. The drug release system also includes at least one drug which is incorporated into the polymeric drug-enriched phase wherein the drug-enriched phase comprises sites within the bulk polymer phase that are continuous in both cross-section and longitudinal directions. Other embodiments of the device include implantable devices, such as a stent, catheter or guidewire, to which the drug release system is attached or adhered.

Another embodiment of the present invention includes a method for making a device for a continuous release of drugs. The method comprises providing a bulk phase polymer and providing a drug that is substantially insoluble in the bulk phase polymer. The method also includes providing a drug enriched polymer. The drug enriched polymer is substantially insoluble in the bulk polymer. One or more of the drugs are soluble in the drug-enriched polymer. The method further comprises providing a solvent. The bulk phase polymer, the drug enriched polymer and the drug or drugs are blended in the solvent so that the drug or drugs are incorporated into the drug receiving polymer and the drug enriched polymer is dispersed within the bulk polymer.

DETAILED DESCRIPTION

One embodiment of the present invention includes a drug release system comprising two or more polymers that are insoluble in each other. The polymers are blended in a solvent to form two polymer phases which create a polymer blend. At least one drug is added to the polymer blend. The drug or drugs are soluble in one of the polymer phases, hereinafter referred to as the "drug-enriched polymer" or "drug enriched polymer phase." The polymer blend with the drug enriched polymer phase is removed from the solvent and is allowed to set. Once set, this drug release system has a morphology that has a predictable and preselectable drug release profile with desirable film properties. The desirable film properties include adherence or attachment to a polymeric or metal surface of an implantable device. Thus, the drug release system serves a dual function of predictable, preselectable drug delivery and coating an implantable device.

The term "preselectable" as used herein refers to an ability to preselect one or more drugs to be released. "Preselectable," for some embodiments, also refers to a rate of drug release.

The polymer phase that includes the soluble drug, the drug-enriched polymer phase, preferably has a glass transition temperature, Tg, less than human body temperature of about 37 degrees Centigrade. This polymer phase shall be referred to herein as a "drug-enriched polymer." Upon incorporating one or more drugs into the polymer, the polymer is kept at a temperature that is lower than the glass transition temperature. The term "glass transition temperature" as used herein refers to a temperature at which the polymer chain undergoes long range motion characterized by a transition from a glassy state to a rubbery state. The glass transition temperature is also the temperature at which the rate of diffusion within the polymer phase changes by several orders of magnitude as the polymer goes from the glassy state to the rubbery state.

A polymer with a Tg that is less than 37 degrees Centigrade is used as the drug-enriched polymer because the diffusion rate of molecules, such as drug molecules within the polymer, decreases one to two orders of magnitude when the polymer is exposed to a temperature that is below the Tg. The Tg features of the drug enriched polymer impart to the polymer features that allow additional control of the drug delivery rate. For instance, when the polymer is at a temperature below its Tg, it will not be within a living being, such as a human being. At these lower temperatures, the drug diffusion is suppressed and the drug does not prematurely diffuse through the bulk polymer. This is desirable because outside of a human being, drug diffusion through the polymer is problematic. Once the drug-enriched polymer phase is implanted, the temperature of the polymer approaches its Tg and the rate of diffusion of drug through the polymer increases. The drug or drugs are deliverable to a predetermined site, such as to a lesion in a blood vessel. Once at this site, the drugs diffuse through the drug-enriched polymer. Polymers which can be used as the drug enriched phase include polyethylene oxide, PEO, and poly n-vinyl pyrrolidone.

The drug enriched polymer is at a concentration greater than the percolation threshold concentration, which is about 33–36%, assuming a morphology of spherical domains, to form a continuous drug enriched phase within the bulk polymer film. The term "percolation threshold" as is used herein refers to a state achieved when an aqueous drug enriched phase forms a continuous, interconnecting network throughout the bulk polymer thickness. The continuous drug enriched phase is one where the drug-enriched polymer phase is substantially uniformly distributed within the bulk phase, such as is shown generally, in one perspective view, at 10, in FIG. 1.

The continuous drug-enriched polymer phase, is illustrated at 11 in FIG. 1, for one embodiment. The bulk polymer 12 forming the phase which is not drug-enriched, referred to herein as the "bulk phase" or "bulk matrix" has acceptable film properties. One suitable polymer for use in the drug release system, as a bulk phase polymer, is poly (ethylene-co-vinyl) alcohol, which is also known as EVAL. EVAL is a thermoplastic polymer, manufactured by EVAL Company of America (EVALCA), of Lisle, Ill. This polymer 12 has a formulation which is the following:

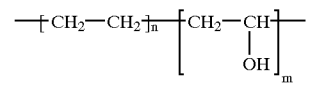

The drug-enriched polymer containing the drug has, for one embodiment, the formula:

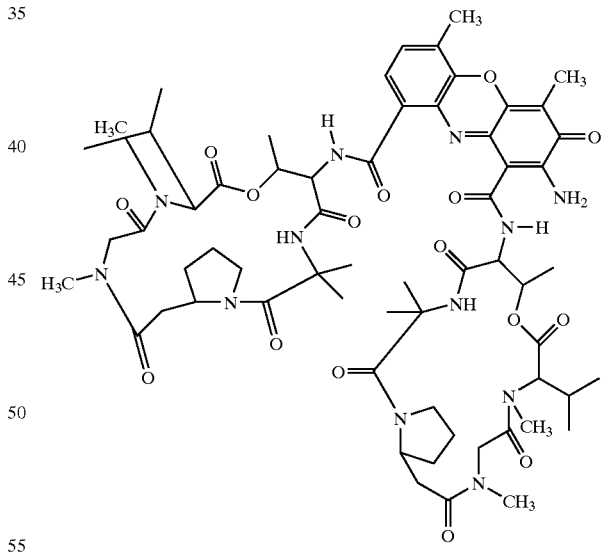

One drug delivery system is composed of two components: one, a hydrophobic component, including but not limited to poly(ethylene-co-vinyl alcohol), and two, a hydrophilic component, which includes but is not limited to polyethylene glycol. The dissimilarity of solubility parameters of the components results in a phase separation of the two polymer phases. The two polymers are blended in a common solvent, such as dimethyl sulfoxide or N,N-dimethylacetamide, to form a solution. At least one therapeutic drug is added to the solution, such as the therapeutic drug, actinomycin D. However, the therapeutic drug or drugs are not limited to the antiproliferative class of drugs which has preferential solubility in the hydrophilic phase.

For some embodiments, the drug delivery system comprising the drug and polymer solution is applied to an implantable device to form a coating on the device. The coated device is dried to remove the solvent, by vacuum or by convection processing. The drying allows the polymers within the applied solution to form phases and to separate. Once dried, the coating retains flexibility.

If the volume percent of the drug enriched hydrophilic phase is less than about 30%, the hydrophilic polymer and drug will exhibit a discontinuous pore structure, as shown at 10 in FIG. 1. The discontinuous pore structure shown in FIG. 1 is defined as being below the percolation threshold.

If the volume percent of the drug enriched hydrophilic phase is greater than about 30%, the hydrophilic polymer and drug will exhibit a pore structure 22 that is continuous throughout the volume of the bulk polymer 24, as shown generally at 20 in FIG. 2. The continuous pore structure 22 within the bulk polymer volume of the polymer 24 is defined as being above the percolation threshold.

The elution of the drug from a drug release coating, such as is shown in FIG. 1, below the percolation threshold, is dependent upon the diffusion of the drug within the drug-enriched polymer 11 through the hydrophobic bulk polymer 12. This is contrary to the diffusion of the drug from a drug release coating above the percolation threshold, such as is illustrated in FIG. 2, which is dependent upon the diffusion of the drug from the pore network 22, and upon the mean pore length.

Common solvents and co-solvents usable for the blending of the polymers include dimethyl sulfoxide, N,N-dimethylacetamide, dimethyl sulfoxide-tetrahydrofuran, and isopropanol-water.

Once the polymers are blended and the drug is incorporated in the drug-enriched polymer, the solvent is evaporated. The evaporation is carried out, for some embodiments, at a reduced pressure and at a temperature that is as close to ambient temperature as possible.

Examples of such drugs include antiproliferative substances as well as antineoplastic, anti-inflammatory antiplatelet, anticoagulant, antifigrin, antithrombin, antimitotic, antibiotic, antioxidant, and combinations thereof. A suitable example of an antiproliferative substance includes actinomycin D, or derivatives and analogs thereof, manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin I1, actinomycin X1, and actinomycin C1. Examples of suitable antineoplastics include paclitaxel and docetaxel. Examples of suitable antiplatelets, anticoagulants, antifibrins, and antithrombins, include sodium heparin, low molecular weight heparin, hirudin, argatroban, forskolin, vapisprost, prostacyclin and prostacyclin analogs, dextran, D-phe-pro-arg-chloromethylketone (synthetic antithrombin), dipyridamole, glycoprotein Iib/IIIa platelet membrane receptor antagonist, recombinant hirudin, thrombin inhibitor, available from Biogen, and 7E–3B, an antiplatelet drug from Centocore. Examples of suitable antimitotic agents include methotrexate, azathioprine, vincristine, vinblastine, antiproliferative agents include angiopeptin (a somatostatin analog from Ibsen), angiotensin converting enzyme inhibitors such as CAPTOPRIL, available from Squibb, CILAZAPRIL, available form Hoffman-LaRoche, or LISINOPRIL, available form Merck, calcium channel blockers such as Nifedipine, colchicine, fibroblast growth factor (FGF) antagonists, fish oil, omega 3-fatty acid, histamine antagonists, LOVASTATIN, an inhibitor of AMG-CoA reductase, a cholesterol lowering drug from Merck, a cholesterol lowering drug, monoclonal antibodies such as PDGF receptors, nitroprusside, phosphodies terase, inhibitors, prostaglandin inhibitor, Seramin, a PDGF antagonist, serotonin blockers, steroids, thioprotease inhibitors, triazolopyrimidine, a PDGF antagonist, and nitric oxide. Other therapeutic substances or agents which may be appropriate include alpha-interferon, genetically engineered epithelial cells, and dexamethasone.

In another embodiment, the drug delivery system comprises a polymer film doped with one or more therapeutic drugs. The polymer film is comprised of a graft copolymer, the copolymer having segments that differ significantly in their solubility parameters. The solubility differences result in phase separation of the two segments. In this embodiment, the hydrophobic polymer is poly(ethylene-co-vinyl alcohol), commercially known as EVAL. In the embodiment, a hydrophilic copolymer such as a polyethylene oxide with a molecular weight between 3200 and 20,000 with an isocyanate functionality is grafted as a side chain, in the following chemical reaction:

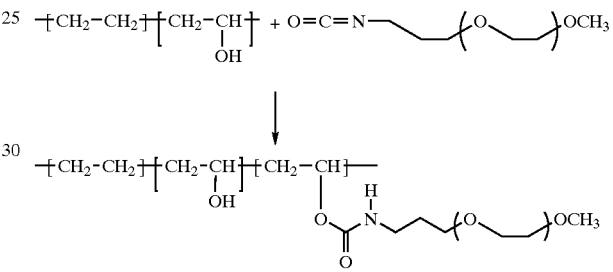

The graft copolymer with a molecular weight of 3200 daltons is functionalized with 0.27 mol percent of the hydroxyl functionalities of the poly(ethylene-co-vinyl alcohol) and has an average of two ethylene oxide polymers grafted to the polymer. The total volume fraction of hydrophilic polymer and drug occupies approximately 35% of the polymer matrix and assumes a cylindrical-like pore morphology. The grafted co-polymer with a molecular weight of 3200 daltons functionalized with 0.68 mole percent of the hydroxyl functionalities has an average of five co-polymer segments attached to any given polymer chain. The hydrophilic graft polymer volume containing the polyethylene oxide functionality and the drug, forming a drug enriched polymer, are present at approximately 50 volume percent. The drug enriched polymer assumes a lamellar structure as is shown at 40c in FIG. 3c.

The morphologies of the drug enriched graft polymer 32 within the bulk polymer substrate 34, are shown at 40a, 40b and 40c, respectively, in FIGS. 3a, 3b and 3c. These different morphologies are due to an increasing concentration of the drug enriched polymer phase 32a, 32b and 32c, respectively, in which one or more drugs is incorporated. At higher concentrations, the drug enriched polymer phase coalesces to form a lamellar morphology. The drug release embodiment 40a, shown in FIG. 3a, is a discontinuous pore structure, with the drug-enriched polymer phase 32a discretely dispersed in the bulk phase 34a.

The drug-enriched polymer structure 32b in FIG. 3b has a semi-continuous phase and in FIG. 3c, the drug-enriched polymer 32c has a continuous phase in which the drug is soluble and diffusible from the continuous phase, when implanted into a living being. The semi-continuous phase 32b comprises sites that are discrete in cross-section but continuous in a longitudinal direction, as is shown in FIG. 3b. The continuous phase 32c, shown in FIG. 3c, defines a channel 33c in which the drug is diffusible from the bulk polymer 34c to the polymer interface 35. The drug-enriched sites are continuous in both cross-section and in a longitudinal direction.

EXAMPLE 1

One exemplary composition that produces the drug release morphology of FIG. 3c includes an EVAL polymer with 56 weight percent ethylene groups, 43.32 weight percent vinyl alcohol functionalities and 0.68 weight percent vinyl ether groups. The weight percent refers to the percent of the total drug release system weight. The vinyl ether groups are functionalized with PEO-isocyanate, which forms a urethane linkage, using groups that have a molecular weight of a side group of 3200 g/mol. The side groups comprise 33 weight percent of the total EVAL/PEO polymer. The composition of the PEO-isocyanate blend is 75 weight percent functionalized EVAL and 25 weight percent drug. This composition gives rise to a 50 weight percent hard, bulk phase and a 50 weight percent drug/PEO side chain phase. The final structure is a lamellar structure.

The chemical reaction is as follows:

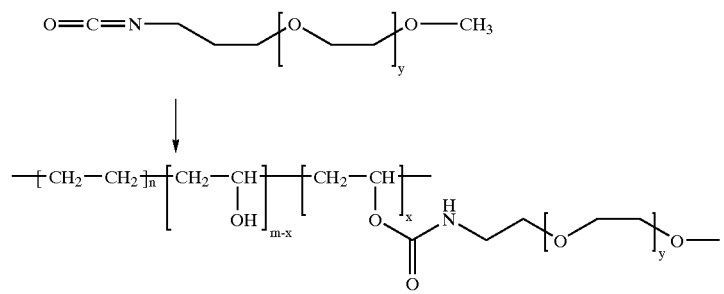

(x)=66 weight %; (y)=44 weight %. M is approximately equal to 70 units. Molecular weight is approximately 3200 units. With the drug release system such as is shown at 40c in FIG. 3c, drug release is substantially continuous within a human being.

The drug release system of the present invention is deliverable to a treatment site by attachment to a device such as a stent or catheter or guidewire. For other embodiments, the drug release system is encapsulated and ingested or subcutaneously injected. For other embodiments, the drug release system is adhered to a prosthetic device or a graft or other implantable device by methods known to those skilled in the art.

Once positioned within a living being by one of the implantable devices, the drug release system commences delivering drugs because the polymer component of the drug-laden phase is at a temperature below its glass transition temperature. The release of drugs is substantially continuous.

While specified embodiments of the invention have been herein described, it is to be appreciated that various changes, rearrangements and modifications may be made therein without departing from the scope of the invention as defined by the appended claims.

What is claimed is:

1. A drug release system comprising:
   a bulk polymer phase;
   a polymeric drug-enriched phase within the bulk polymer phase, the polymeric drug-enriched phase being substantially or completely insoluble in the bulk polymer phase; and
   a drug incorporated into the drug-enriched phase, the drug having preferential solubility for the polymeric drug-enriched phase than the bulk polymer phase wherein, the bulk polymeric phase is substantially or completely devoid of the drug.

2. The drug release system of claim 1 wherein the drug-enriched phase comprises sites within the bulk polymer phase that are not interconnecting.

3. The drug release system of claim 1 wherein the drug-enriched phase comprises sites within the bulk phase tat are intermittent in cross-section and continuous in a longitudinal direction.

4. The drug release system of claim 1 wherein the drug-enriched phase comprises sites within the bulk phase that are continuous in both cross-section and in a longitudinal direction.

5. The drug release system of claim 1 wherein the bulk phase comprises poly(ethylene-co-vinyl)alcohol.

6. The drug release system of claim 1 wherein the bulk phase comprises polyethylene glycol.

7. The drug release system of claim 1 wherein the drug-enriched phase comprises polyethylene oxide and at least one drug.

8. The drug release system of claim 1 wherein the drug-enriched phase comprises poly n-vinyl pyrrolidone and at least one drug.

9. The drug release system of claim 1 wherein the drug-enriched phase has a glass transition temperature that is less than the temperature of the living human body.

10. The drug release system of claim 1 wherein the drug-enriched phase has drug concentration that is greater than the percolation threshold.

11. The drug release system of claim 1 wherein the drug comprises Actinomycin D.

12. The drug release system of claim 1 wherein the drug comprises one or more of an antiproliferative substance, an antineoplastic substance, an anti-inflammatory, anti-platelet, anticoagulant, antifibrin, antithrombin, antimitotic, antibiotic, antioxidant and combinations of these substances.

13. A drug release system for a stent, comprising:
    a first polymer;
    a second polymer combined with the first polymer, the second polymer being significantly or completely insoluble in the first polymer; and
    a therapeutic substance having a greater degree of solubility in the second polymer than the first polymer such that all of or a significant amount of the therapeutic substance is distributed in the second polymer but not the first polymer.

14. The system of claim 13, wherein the second polymer has a glass transition temperature less than 37° C.

15. The system of claim 13, wherein the second polymer constitutes less than about 30% by volume of the total volume of the first polymer plus the second polymer.

16. The system of claim 13, wherein the second polymer constitutes more than about 30% by volume of the total volume of the first polymer plus the second polymer.

* * * * *